(12) United States Patent
Krayenbuhl

(10) Patent No.: US 9,636,350 B2
(45) Date of Patent: May 2, 2017

(54) PHARMACEUTICAL COMPOSITION FOR USE IN NASAL ADMINISTRATION CONTAINING CORTICOID, AND A QUINOLONE OR FUSIDIC ACID

(75) Inventor: Matthew Krayenbuhl, Pully (CH)

(73) Assignees: Matthew Krayenbuhl, Pully (CH); Antonio Dos Santos, Belmont-sur-Lausanne (CH); Michael Kenyon, Epalinges (CH)

( * ) Notice: Subject to any disclaimer, the term of this patent is extended or adjusted under 35 U.S.C. 154(b) by 0 days.

(21) Appl. No.: 14/006,414

(22) PCT Filed: Mar. 19, 2012

(86) PCT No.: PCT/IB2012/051310
§ 371 (c)(1),
(2), (4) Date: Nov. 26, 2013

(87) PCT Pub. No.: WO2012/127407
PCT Pub. Date: Sep. 27, 2012

(65) Prior Publication Data
US 2014/0296192 A1    Oct. 2, 2014

(30) Foreign Application Priority Data
Mar. 21, 2011    (EP) .................................... 11159067

(51) Int. Cl.
| | | |
|---|---|---|
| *A61K 31/58* | (2006.01) | |
| *A61K 9/00* | (2006.01) | |
| *A61K 9/12* | (2006.01) | |
| *A61K 45/06* | (2006.01) | |
| *A61K 31/47* | (2006.01) | |
| *A61K 31/56* | (2006.01) | |
| *A61K 31/575* | (2006.01) | |
| *A61K 31/496* | (2006.01) | |
| *A61K 31/573* | (2006.01) | |

(52) U.S. Cl.
CPC ............ *A61K 31/58* (2013.01); *A61K 9/0043* (2013.01); *A61K 9/12* (2013.01); *A61K 31/47* (2013.01); *A61K 31/496* (2013.01); *A61K 31/56* (2013.01); *A61K 31/573* (2013.01); *A61K 31/575* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,844,902 A | 7/1989 | Grohe | |
| 2001/0049366 A1 | 12/2001 | Singh et al. | |
| 2006/0051300 A1* | 3/2006 | Chaudry | ........................ 424/46 |
| 2007/0148192 A1 | 6/2007 | Laddha et al. | |
| 2010/0087409 A1* | 4/2010 | Freehauf et al. | ............. 514/171 |
| 2011/0281830 A1 | 11/2011 | Sulur et al. | |

FOREIGN PATENT DOCUMENTS

| | | |
|---|---|---|
| WO | WO 2004/087043 | 10/2004 |
| WO | WO 2009/027762 | 3/2009 |
| WO | WO 2010/084457 | 7/2010 |

OTHER PUBLICATIONS

JAMA Letters to the Editors (herein identified as JAMA Letters) (Antibiotics and Nasal Steroids for Acute Sinusitis, JAMA Mar. 26, 2008, 1422-1423 vol. 299 No. 12).*
Saravolatz et al. (Reviews of Anti-Infective Agents, CID 2003:37 (Nov. 1) pp. 120-1215).*
International Search Report for PCT/IB2012/051310 mailed Jul. 2, 2012.
Paganelli, Fernando, et al., "A Single Intraoperative Sub-Tenon's Capsule Injection of Triamcinolone and Ciprofloxacin in a Controlled-Release System for Cataract Surgery," Investigative Ophthalmology & Visual Science, Jul. 2009, vol. 50, No. 7, pp. 3041-3047.
Inquiry of the substantive examination dated Mar. 16, 2016, issued in Russian Patent Application No. 2013144043/15(067946) and English translation.

* cited by examiner

Primary Examiner — Kortney L Klinkel
Assistant Examiner — William Lee
(74) Attorney, Agent, or Firm — Nixon & Vanderhye P.C.

(57) ABSTRACT

The invention relates to a pharmaceutical composition of unit dose for inhalation by a human subject comprising a topical corticoid and a quinolone or fucidic acid, characterized in that the ratio of the weight of the topical corticoid to the weight of the quinolone or fucidic acid is between 0.02 and 20 and the amount of quinolone or of fucidic acid is less than 1 mg. This composition can be administered by nasal spray and is used for treating the upper and lower respiratory tract, in particular sinusitis and nasal polyps.

23 Claims, No Drawings

PHARMACEUTICAL COMPOSITION FOR USE IN NASAL ADMINISTRATION CONTAINING CORTICOID, AND A QUINOLONE OR FUSIDIC ACID

This application is the U.S. national phase of International Application No. PCT/IB2012/051310 filed 19 Mar. 2012 which designated the U.S. and claims priority to EP 11159067.5 filed 21 Mar. 2011, the entire contents of each of which are hereby incorporated by reference.

FIELD OF THE INVENTION

The present invention relates to compositions of unit dose comprising a topical corticoid and an antibiotic selected from the quinolone class or an antibiotic such as fusidic acid.

These compositions can be used advantageously—but not exclusively—in the treatment of sinusitis.

PRIOR ART

Compositions such as those described above are notably disclosed in international patent application WO 03/020219, European patent application EP 1 894 559 A1 and U.S. Pat. No. 7,691,094 B2.

GENERAL DESCRIPTION OF THE INVENTION

The problem that the present invention aims to solve is improvement of the treatments currently offered, in particular treatments for sinusitis. Improvement means "increased efficacy of the treatment and/or decrease in toxicity and/or minimization of the amounts used (e.g. of antibiotic)".

In the invention, the solution of the aforementioned problem consists of a pharmaceutical composition of unit dose for inhalation by a human subject in which the corticoid/antibiotic ratio is particularly high in comparison with what is observed in the compositions of the prior art. We have surprisingly found that a topical corticoid/quinolone or fusidic acid ratio between 0.02 and 20 with an amount of quinolone or of fusidic acid less than 1 mg exhibits the best results on a human subject.

More precisely, the invention relates to a pharmaceutical composition of unit dose for inhalation by a human subject comprising at least one topical corticoid and a quinolone or fusidic acid, characterized in that the ratio between the weight of the topical corticoid and the weight of the quinolone or of fusidic acid is between 0.02 and 20 and the amount of quinolone or of fusidic acid is less than 1 mg.

More particularly, the ratio of the weight of the topical corticoid to the weight of the quinolone or of fusidic acid is between 0.4 and 2 and the amount of quinolone or of fusidic acid is between 10 and 400 µg; more preferably the ratio of the weight of the topical corticoid to the weight of the quinolone or of fusidic acid is between 0.5 and 1.5 and the amount of quinolone or of fusidic acid is between 70 and 150 µg.

A unit dose is the amount of a pharmaceutical composition administered to a patient in a single dose, such as a puff of nasal spray.

The pharmaceutical composition of unit dose according to the invention comprises a first active ingredient selected from the topical corticoids. These corticoids (also called steroids, corticosteroids, glucocorticoids or cortisone analogues) are compounds that are generally used for local application (nasal, cutaneous, ophthalmic, etc.). Examples of these topical corticoids include: mometasone furoate, budesonide, beclometasone, fluticasone furoate, fluticasone propionate, triamcinolone.

The preferred corticoid is budenoside and triamcinolone.

The pharmaceutical composition of unit dose according to the invention further comprises a second active ingredient selected from the quinolones. The quinolones form a class of antibiotics. Examples of said quinolones include norfloxacin, ofloxacin, ciprofloxacin, lomefloxacin, lexofloxacin.

The preferred quinolone is ciprofloxacin.

The second active ingredient can also be fusidic acid.

In a preferred embodiment of the invention, the pharmaceutical composition of unit dose according to the invention comprises fluticasone furoate and ciprofloxacin.

In another preferred embodiment of the invention, the pharmaceutical composition of unit dose according to the invention comprises budesonide and ciprofloxacin.

In another preferred embodiment of the invention, the pharmaceutical composition of unit dose according to the invention comprises triamcinolone and ciprofloxacin.

The pharmaceutical composition of unit dose according to the invention can also comprise one or more pharmaceutically acceptable excipients. These excipients can be selected from dispersants, solubilizers, stabilizers, preservatives, antioxidants, etc. As an example, the pharmaceutical composition of unit dose according to the invention can comprise mannitol and/or benzalkonium chloride. It can also comprise potassium sorbate, anhydrous glucose, dispersible cellulose, polysorbate 80, disodium edetate.

The pharmaceutical composition of unit dose according to the invention is more particularly intended for treatment of the upper and lower respiratory tract. It is sprayable and is suitable for packaging in the form of nasal spray, metered dose ranging from 20 µl to 400 µl, most preferred 100 µl.

The upper respiratory tract (or upper airways) is extrathoracic and comprises the nose and the nasal fossae, the mouth, the pharynx (respiratory/digestive junction) and the larynx (throat).

The lower respiratory tract (or lower airways) is intrathoracic and comprises the conduction and transition zone (extrapulmonary tract (trachea), intrapulmonary tract (principal bronchi, lobar bronchi, bronchioles) and the respiratory zone (alveolar ducts and sacs, pulmonary alveoli).

The pharmaceutical composition of unit dose according to the invention is advantageously formulated as a liquid (solution, suspension, emulsion, etc.) in unit dose or in a multi-dose bottle for administration by spray in the nasal cavity and the sinuses for treatment of the respiratory passages. This composition includes a powder that can be mixed with a diluent to produce a liquid.

The composition of unit dose according to the invention is used in the treatment of the upper respiratory tract, notably in the treatment of sinusitis, in particular of acute or chronic sinusitis, and nasal polyps and delivered to the nose through a metered spray with volumes ranging from 20 µl to 400 µl, most preferred 100 µl.

The pharmaceutical composition of unit dose according to the invention is used in the treatment of the upper respiratory tract, notably in the treatment of mucoviscidosis.

The composition of unit dose according to the invention, for which the ratio of the weight of topical corticoid to the weight of quinolone or fusidic acid is between 0.02 and 8 and the amount of quinolone or of fusidic acid is less than 1 mg, is more particularly used for treatment of the lower respiratory tract.

The invention also relates to a pharmaceutical preparation containing several unit doses according to the invention and being in the form of nasal spray.

The invention further relates to a dose of the pharmaceutical composition according to the invention intended for use for one day and for one nostril comprising 50 µg to 300 µg of topical corticoid and from 150 to 400 µg of quinolone.

The invention further relates to the use of the composition of unit dose according to the invention for treatment of the respiratory passages, said composition having to be administered in the form of spray twice, consecutively, in each nostril, once or twice a day.

DETAILED DESCRIPTION OF THE INVENTION

The invention is described in more detail below, by means of examples:

A pharmaceutical composition of unit dose comprising budesonide and ciprofloxacin in a ratio of 1.34 was administered by nasal spray, each unit dose or puff of nasal spray delivering 125 µg of budesonide and 93 µg of ciprofloxacin. The composition further comprises at least mannitol and benzalkonium chloride as excipients. A dose of two sprays per nostril per day was prescribed for each patient. One puff of nasal spray corresponds to about 100 µL of liquid.

A pharmaceutical composition of unit dose comprising budenoside and ciprofloxacin in a ratio of 0.67 was also administered by nasal spray, each unit dose or puff of nasal spray delivering 62.5 µg of budenoside and 93 µg of ciprofloxacin. The composition further comprises at least mannitol and benzalkonium chloride as excipients. A dose of two sprays per nostril per day was prescribed for each patient.

A pharmaceutical composition of unit dose comprising fluticasone furoate and ciprofloxacin in a ratio of 0.4 was also administered by nasal spray, each unit dose or puff of nasal spray delivering 30 µg of fluticasone furoate and 75 µg of ciprofloxacin. The composition further comprises at least mannitol and benzalkonium chloride as excipients. A dose of two sprays per nostril per day was prescribed for each patient.

A pharmaceutical composition of unit dose comprising budenoside and fusidic acid in a ratio of 1 was also administered by nasal spray, each unit dose or puff of nasal spray delivering 150 µg of budenoside and 150 µg of fusidic acid. The composition further comprises at least mannitol and benzalkonium chloride as excipients. A dose of two sprays per nostril per day was prescribed for each patient.

A pharmaceutical composition of unit dose comprising triamcinolone and ciprofloxacin in a ratio of 0.5 was also administered by a puff of nasal spray (100 µl) delivering 37.5 µg of triamcinolone and 75 µg of ciprofloxacin.

A pharmaceutical composition of unit dose comprising triamcinolone and ciprofloxacin in a ratio of 0.44 was also administered by a puff of nasal spray (100 µl) delivering 38.8 µg of triamcinolone and 88.4 µg of ciprofloxacin.

About 500 patients with acute or chronic sinusitis (with or without nasal polyps) were tested with daily treatment for 10 days to 8 weeks. A positive effect was observed and a very notable improvement was observed in a vast majority of cases.

It goes without saying that the invention is not limited to the examples described above.

The invention claimed is:

1. A pharmaceutical composition of unit dose for inhalation as a nasal spray by a human subject for treatment of sinusitis comprising:
   at least one topical corticoid, and
   a quinolone or fusidic acid,
   wherein the ratio of the weight of the topical corticoid to the weight of the quinolone or the fusidic acid is between 0.02 and 20,
   wherein the amount of quinolone or fusidic acid is less than 1 mg,
   wherein the unit dose is from 20 µl to 400 µl,
   wherein the unit dose is for inhalation as a human nasal spray for treatment of sinusitis, and
   wherein the unit dose is in a dose metered device.

2. The pharmaceutical composition of unit dose according to claim 1, in which the ratio of the weight of the topical corticoid to the weight of the quinolone or the fusidic acid is between 0.4 and 2, and the amount of quinolone or fusidic acid is between 10 and 400 µg.

3. The pharmaceutical composition of unit dose according to claim 2, in which the ratio of the weight of the topical corticoid to the weight of the quinolone or the fusidic acid is between 0.5 and 1.5, and the amount of quinolone or fusidic acid is between 70 and 150 µg.

4. The pharmaceutical composition of unit dose according to claim 3, in which the ratio of the weight of the topical corticoid to the weight of the quinolone is 1.34, and the amount of quinolone is 93 µg.

5. The pharmaceutical composition of unit dose according to claim 3, in which the ratio of the weight of the topical corticoid to the weight of the quinolone is 1, and the amount of quinolone is 75 µg.

6. The pharmaceutical composition of unit dose according to claim 3, in which the ratio of the weight of the topical corticoid to the weight of the quinolone is 0.5, and the amount of quinolone is 75 µg.

7. The pharmaceutical composition of unit dose according to claim 1, in which the topical corticoid is selected from the group of the following molecules: mometasone furoate, budesonide, beclomethasone, fluticasone furoate, fluticasone propionate and triamcinolone.

8. The pharmaceutical composition of unit dose according to claim 1, in which the quinolone is selected from the group of the following molecules: ofloxacin, norfloxacin, ciprofloxacin, lomefloxacin and levofloxacin.

9. The pharmaceutical composition of unit dose according to claim 7 in which the corticoid is fluticasone furoate and the quinolone is ciprofloxacin.

10. The pharmaceutical composition of unit dose according to claim 7 in which the corticoid is triamcinolone and the quinolone is ciprofloxacin.

11. The pharmaceutical composition of unit dose according to claim 1, further comprising a pharmaceutically acceptable excipient.

12. The pharmaceutical composition of unit dose according to claim 1 in which the ratio of the weight of the topical corticoid to the weight of the quinolone is between 0.25 and 1, the amount of quinolone is between 75 µg and 100 µg, the topical corticoid is fluticasone furoate and the quinolone is ciprofloxacin, the excipients are at least mannitol and benzalkonium chloride.

13. The pharmaceutical composition of unit dose according to claim 1, in which the ratio of the weight of the topical corticoid to the weight of the quinolone is between 0.25 and 1, the amount of quinolone is between 75 µg and 100 µg, the topical corticoid is triamcinolone and the quinolone is ciprofloxacin, the excipients are at least mannitol and benzalkonium chloride.

14. The pharmaceutical composition of unit dose according to claim 1 for use in the treatment of the upper respiratory tract.

15. The pharmaceutical composition of unit dose according to claim 14 for use in the treatment of sinusitis.

16. The pharmaceutical composition of unit dose according to claim 1 for use in the treatment of the lower respiratory tract.

17. The pharmaceutical composition of unit dose according to claim 16 for use in the treatment of mucoviscidosis.

18. The pharmaceutical preparation containing several unit doses according to claim 1, wherein it is in the form of nasal spray.

19. A dose of the pharmaceutical composition according to claim 1 intended for use for one day and for one nostril comprising 50 to 300 μg of topical corticoid and from 150 to 400 μg of quinolone.

20. A method of using the pharmaceutical composition of unit dose for inhalation as a nasal spray by a human subject for treatment of sinusitis according to claim 1 for, wherein said use comprises:
   selecting said pharmaceutical composition, and
   administering said pharmaceutical composition in the form of the nasal spray twice in each nostril of the human at a rate of once or twice a day, to treat sinusitis of the human.

21. The pharmaceutical composition of unit dose according to claim 11, wherein the pharmaceutically acceptable excipient is mannitol and/or benzalkonium chloride.

22. The pharmaceutical composition of unit dose according to claim 15, wherein the sinusitis is acute sinusitis or chronic sinusitis.

23. The pharmaceutical composition of unit dose according to claim 1 for use in the treatment of the upper respiratory tract and the lower respiratory tract.

* * * * *